March 26, 1974 A. BARBERET Plant Pat. 3,533
CARNATION PLANT
Filed Dec. 11 1972
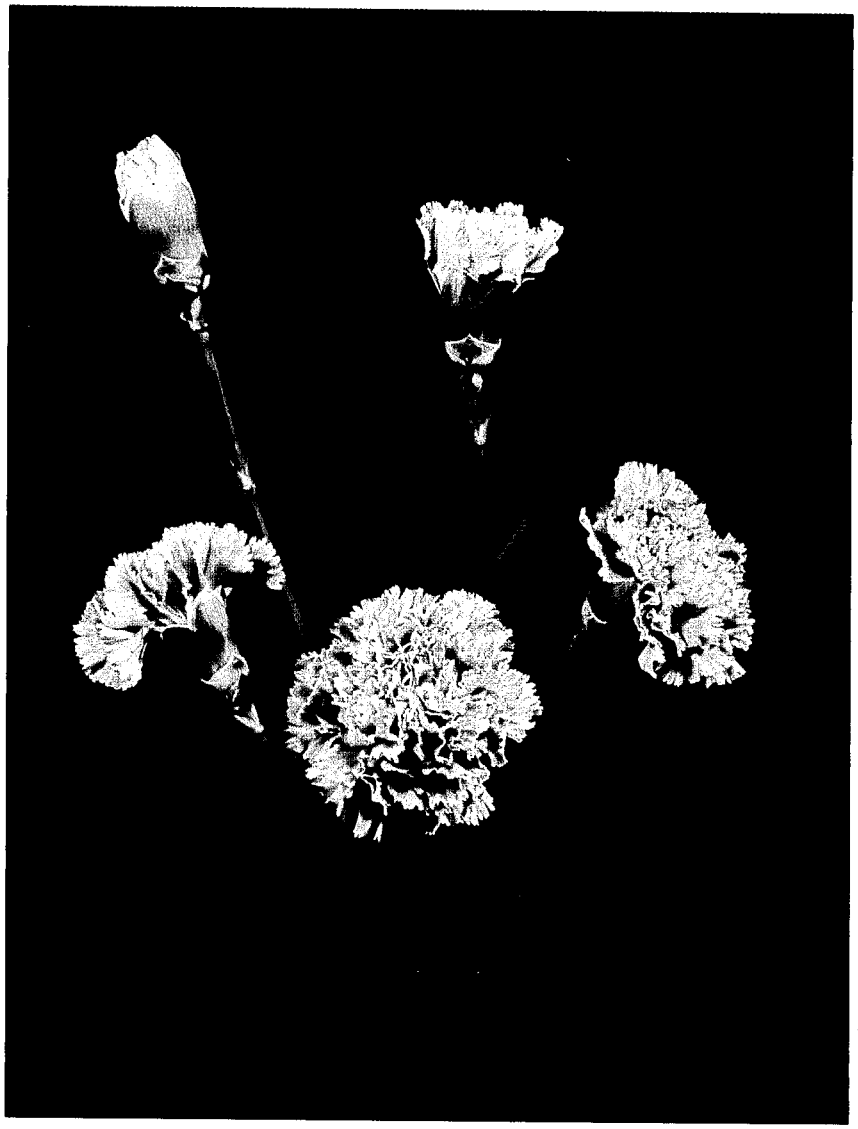

United States Patent Office

Plant Pat. 3,533

Patented Mar. 26, 1974

3,533

CARNATION PLANT

Alexandre Barberet, La Londe, France, assignor to Laboratoire de Physiologie Vegetale de La Londe, Societe Civile, La Londa, France Filed Dec. 11, 1972, Ser. No. 313,747
Claims priority, application Italy, Dec. 23, 1971, 32,849/71
Int. Cl. A01h 5/00
U.S. Cl. Plt.—70 1 Claim

ABSTRACT OF THE DISCLOSURE

A new variety of carnation plant originating as a seedling hybrid of two selected varieties and characterized by its improved habits of growth and productivity, as compared with Orchid Beauty (unpatented), and the more red-purple color of its blooms.

BACKGROUND OF THE NEW PLANT

This carnation variety was developed by me in 1968 at La Londe, France, as a seedling hybrid of two unnamed and unpatented varieties of Dianthus Caryophyllus identified in my records as 6V1 for the seed parent and 148P for the pollen parent. This seedling was selected for propagation and trial because of its apparent advantage of improved habits of growth and productivity and the particular red-purple color of the flowers. Subsequent propagation by cuttings, under my direction, at La Londe, France, has demonstrated that the expected advantageous characteristics are present in all succeeding generations and appear to be firmly fixed. Commercial scale propagation of this new variety of carnation is now being carried on at La Londe, France, and at West Hartford, Connecticut.

DESCRIPTION OF THE DRAWINGS

My new variety of carnation plant is illustrated by the accompanying color drawing which was reproduced photographically to show the color characteristics of the flower as nearly true as it is reasonably possible to obtain by conventional commercial photographic procedures.

DESCRIPTION OF THE NEW PLANT

The following is a detailed description of my new carnation variety with the color designations according to The RHS Colour Chart published by The Royal Horticultural Society at London, England.

*The plant*

Origin: Seedling.
Parentage:
*Seed parent.*—Carnation 6V1 (unnamed, unpatented).
*Pollen parent.*—Carnation 148P (unnamed, unpatented).
Classification:
*Botanic.*—Hybrid Dianthus Coryophyllus.
*Commercial.*—Carnation for cut flowers.
Form: Bush, as in Sim types.
Height: About 45 cm.
Growth: Erect and vigorous with normal upright branching.
Foliage: Quantity—abundant.
*Leaf shape.*—Lanceolate and up to 10.4 cm. long.
*Texture.*—Smooth.
*Color.*—Upper side—Green Group 133C and 138D. Underside—Green Group 133C and 138D.
Ribs: Axial.
Petioles: None. Leaf is amplexicaul.

*The bud*

Form: Ovoid.
Size: Medium: Diameter: 28 mm.
Opening: Bud opens slowly.
Color: Light Green when sepals first divide and when the petals begin to unfurl.
Sepals: Curl back.
*Color.*—Inside—Pale Green. Outside—Light Green.
Calyx: Large, pear shaped, and does not split.
*Aspect.*—Smooth.

*The flower*

Blooming habit: Plant blooms profusely and continuously.
Size of bloom: Medium, 7.7 to 9 cm. in diameter and 4.5 cm. in depth.
Borne: Single, after disbudding.
Shape: High center.
Petalage: Number of petals—57 to 85, average about 68.
*Form.*—Fan shaped.
*Arrangement.*—Imbricated.
*Color.*—Outer petal—Red-Purple 72C–D to 74D. Base—Red-Purple 72C. Inside petal—Red-Purple 72C–D, 73D and 74D. Reverse side—Red-Purple 73D.
*Appearance.*—Satiny.
Petaloids: About 10 in number.
*Size.*—About one-half the size of normal petals.
*Color.*—Red-Purple.
Persistence: Blooms hang on and dry.
Fragrance: Perceptible.
Effect of weather: Blooms are not affected by wet or hot weather.
Lasting quality:
*On plant.*—15 days.
*As cut flower.*—10 days.
Disease resistance: Plant resists *Fusarium coseum* as observed in areas where it has been grown.

*Reproductive organs*

Stamens:
*Anthers.*—Arranged singly, 2 to 3 mm. long, averaging about 10 in number.
*Filaments.*—2.5 cm. long. Color—White.
*Pollen.*—Yellowish in color.
Pistils: 2 in number. 4 cm. long.
*Stigmas.*—Whitish in color.
Ovaries: Cone shaped.

*Fruit*

Fertility: A little in summer.
Shape: Oblong.
Color: Greenish at maturity.

This new variety of carnation plant most resembles Orchid Beauty (Plant Pat. 193) and its particular advantages reside in its material improvement over Orchid Beauty in both growth and productivity, the more red-purple color of its blooms and the larger flower than that of Orchid Beauty, its early production capability, and the absence of splitting.

I claim:

1. The new and distinct variety of carnation plant substantially as herein shown and described, characterized by its improved habits of growth and productivity, the absence of splitting, and the red-purple coloration of its blooms.

No references cited.

ROBERT E. BAGWILL, Primary Examiner